United States Patent [19]
Schneider et al.

[11] Patent Number: 5,902,829
[45] Date of Patent: May 11, 1999

[54] METHOD OF MODULATING MICROCIRCULATION

[75] Inventors: Heinz Schneider, Cordast, Switzerland; Ronald G. Thurman, Chapel Hill, N.C.

[73] Assignee: Novartis Nutrition AG, Berne, Switzerland

[21] Appl. No.: 08/952,806

[22] PCT Filed: May 17, 1996

[86] PCT No.: PCT/EP96/02124

§ 371 Date: Jan. 26, 1998

§ 102(e) Date: Jan. 26, 1998

[87] PCT Pub. No.: WO96/36327

PCT Pub. Date: Nov. 21, 1996

[30] Foreign Application Priority Data

May 18, 1995 [GB] United Kingdom ............... 9510037

[51] Int. Cl.$^6$ ..................... A61K 31/195; A61K 31/70
[52] U.S. Cl. ........................... 514/565; 514/45
[58] Field of Search ............................ 514/45, 565

[56] References Cited

U.S. PATENT DOCUMENTS

| | | | |
|---|---|---|---|
| 5,385,940 | 1/1995 | Moskowitz | 514/565 |
| 5,436,270 | 7/1995 | Wang | 514/565 |
| 5,656,608 | 8/1997 | Schneider et al. | 514/42 |

FOREIGN PATENT DOCUMENTS

| | | |
|---|---|---|
| 0441119 | 8/1991 | European Pat. Off. . |
| 4-282313 | 4/1992 | Japan . |
| 4-330011 | 11/1992 | Japan . |
| 06038708 | 6/1994 | Japan . |

WO 91/09524  7/1991  WIPO .

OTHER PUBLICATIONS

Thurman RG, et al. AASLD Abstract, vol. 22, No. 4, p. 381a (1995).
Coughlan MG, et al. Cardiovascular Research, vol. 27, pp. 1444–1448 (1993).
Richard V. et al. Circulation, vol. 89, pp. 1254–1261 (1994).
Lefer DJ, New Horizons, vol. 3, pp. 105–112 (1995).
Siegfried MR, et al. The Journal of Pharmacology and Experimental Therapeutics, vol. 260, pp. 668–675 (1991).
Menger MD, et al. Wiener Medizinishche Wochenschrift, vol. 143, pp. 148–158 (1993).
Hasselmann M, FR 2713485, Dec. 7, 1993.
Johnson LR, et al. Physiology of the Gastrointestinal Tract, third edition, vol. 1, pp. 267–294.
Kurose I, et al. Circulation Research, vol. 74, pp. 376–382 (1994).
Weyrich AS, et al. Circulation, vol. 86, pp. 279–288 (1992).
Nakanishi K, et al. American Journal of Physiology, vol. 263, pp. H1650–H1658 (1992).

Primary Examiner—Kevin E. Weddington
Attorney, Agent, or Firm—Michael P. Morris

[57] ABSTRACT

The present invention provides, inter alia, use of L-arginine, a precursor of L-arginine and/or physiologically acceptable salts thereof, or of (i) a nitric oxide donor, and/or (ii) a substrate of the nitric oxide synthetase, and/or (iii) a precursor of the said substrate, in the preparation of a medicament or nutritional formulation for the amelioration of micro-circulatory hypo-perfusion, and/or the treatment or prophylaxis of hypoperfusion-reperfusion injury, in patients which have undergone elective surgery, characterized in that the medicament or nutritional formulation is pre-operatively administered to the patient.

17 Claims, No Drawings

METHOD OF MODULATING MICROCIRCULATION

This appln is a 371 of PCT/EP96/02124 filed May 17, 1996.

The present invention relates to a method of modulating the micro-circulation, particularly in patients who have undergone, or are due to undergo, elective surgery.

Disruption of the microvasculature is a key factor in mechanisms of inter alia hepatic, mesenteric and cardiac ischemia-reperfusion injury. Recent in vitro studies using a blood free, low-flow, reflow liver perfusion model have demonstrated that reperfusion injury can be reduced by improving the microcirculation. For example, perfused livers from rats pre-treated with a fish-oil diet showed a marked improvement in microcirculation and a significant reduction in hepatic damage. In addition, it is also known that adenosine, a known vasodilator and an essential component in Caroline Rinse solution, improves survival following liver transplantation.

The present invention provides inter alia, a medicament, pre-operative administration of which to patients due to undergo elective surgery has a prophylactic effect vis-à-vis hypoperfusion-reperfusion injury in numerous micro-circulatory systems.

According to the present invention there is provided the use of L-arginine, a precursor of L-arginine and/or physiologically acceptable salts thereof, in the preparation of a medicament or nutritional formulation for the amelioration of micro-circulatory hypo-perfusion, and/or the treatment or prophylaxis of hypoperfusion-reperfusion injury, in patients which have undergone elective surgery, characterized in that the medicament or nutritional formulation is pre-operatively administered to the patient.

Preferred precursors of L-arginine are either ornithine or glutamine, particularly preferred ornithine.

The present invention further provides a method for the amelioration of micro-circulatory hypo-perfusion, and/or the treatment or prophylaxis of hypoperfusion-reperfusion injury, in patients which have undergone elective surgery, characterized in that L-arginine, a precursor of L-arginine and/or physiologically acceptable salts thereof is pre-operatively administered to the patient.

L-arginine is the substrate for nitric oxide synthetase (NOS), the enzyme responsible for the production of nitric oxide, a highly unstable molecule which inter alia mediates smooth muscle relaxation in vascular tissue. Two forms of this enzyme are known to be present in vivo, an essentially endothelial cell located calcium/NADPH dependant—calmodulin sensitive constitutive form, and an essentially calcium independent form the production/activity of which is induced in response to, for example, endotoxin/cytokinin—mediated metabolic stress. The inducible form of nitric oxide synthetase is located in macrophages and like cells, such as Kupffer and microglial cells in the liver and nervous system respectively.

Endogenous nitric oxide production can also increase blood flow by reducing the number of blood elements adhering to the lumen of the vessel. In high doses, nitric oxide can be cytotoxic and cause oxidative injury.

According to the present invention there is also provided the use of (i) a nitric oxide donor, and/or (ii) a substrate of the nitric oxide synthetase, and/or (iii) a precursor of the said substrate, in the preparation of a medicament or nutritional formulation for the amelioration of micro-circulatory hypo-perfusion, and/or the treatment or prophylaxis of hypoperfusion-reperfusion injury, in patients which have undergone elective surgery, characterized in that the medicament or nutritional formulation is pre-operatively administered to the patient.

There is further provided a method for the amelioration of micro-circulatory hypo-perfusion, and/or the treatment or prophylaxis of hypoperfusion-reperfusion injury, in patients which have undergone elective surgery, characterized in that i) a nitric oxide donor, and/or (ii) a substrate of the nitric oxide synthetase, and/or (iii) a precursor of the said substrate is pre-operatively administered to the patient.

It is preferred that treatment is initiated at least one day prior to surgery and that the medicament or formulation is administered at least over a period of one day prior to surgery in the case that it is to be administered parenterally. In the case of oral or enteral administration it is preferred that the medicament or formulation is administered over a period of from 3 to 10 days prior to surgery, whereby the treatment is initiated between 3–10 days (inclusive) prior to surgery.

As indicated above, the medicament or formulation may be administered in a form suitable for parenteral or enteral administration. The enteral administration route is preferred; particularly contemplated are oral administration, nasal administration and/or tube feeding. The medicament or formulation is conveniently administered in the form of an aqueous liquid. The medicament or formulation in a form suitable for enteral application is accordingly preferably aqueous or in powder form, whereby the powder is conveniently added to water prior to use. For use in tube feeding, the amount of water to be added will depend, inter alia, on the patient's fluid requirements and condition.

The beneficial effect of the use of the medicament or formulation of the present invention for treatment or prophylaxis of hypoperfusion-reperfusion injury, in patients which have undergone elective surgery is due to improvement of the microcirculation in the respective organs.

Greatest improvements in micro-circulations are associated with the mesenteric, gut, hepatic and cardiac circulations accrue from use of the medicament or formulation according to the invention.

The amount of medicament or formulation to be administered depends to a large extent on the patient's specific requirements. In the case that the medicament or formulation comprises L-arginine (or a pharmaceutically acceptable salt thereof) or a precursor of L-arginine, such as ornithine, the patient should be administered enough to increase the plasma total concentration of L-arginine from basal levels of about 70–85 µM to about 100–200 µM, preferably to about 120–150 µM. The plasma total concentration of L-arginine should preferably not be elevated to above about 200 µM, as a consequence of use according to the invention. The medicament or formulation may be so formulated as to deliver to the patient about 1 to about 30 g, preferably 5 to 18 g, of nitric oxide synthetase substrate or L-arginine, a precursor of L-arginine and/or physiologically acceptable salts thereof, per 24 hours, or about 0.1 to about 20 g of nitric oxide donor per 24 hours. It will be appreciated, however, that in particular where the medicament or formulation comprises nitric oxide donors per se, the patient should not be administered so much medicament or formulation that the (cyto)toxic effects of nitric oxide become apparent.

It is particularly preferred that the substrate of the nitric oxide synthetase is L-arginine or a physiologically acceptable salt thereof. In a non endotoxin/cytokinin stressed individual it is to be expected that the substrate is utilized by the calcium and NADPH dependant/calmodulin sensitive constitutive nitric oxide synthetase and accordingly, the invention contemplates this form of the synthetase as the target for the L-arginine contained within the medicament or formulation, or the L-arginine which results from the precursor (such as ornithine or glutamine contained within the medicament or formulation) which is metabolically converted into L-arginine upon ingestion/digestion by the patient.

The nitric oxide donor present in the medicament or formulation may be selected from the group consisting of glycerol trinitrate, isosorbide dinitrate, nitroprusside, 8-bromoguanosine-3,5'-monophosphate, spermine-NO, spermidine-NO, and SIN1.

Angiotensin II is a potent splanchnic vaso-constrictor and is released in increased quantities during surgery that is associated with a high incidence of gut mucosal hypoperfusion. Moreover, non-steroidal anti-inflammatory drugs and free radical scavengers could modulate the degree of gut mucosal hypoperfusion and/or the extent of histological damage consequent upon reperfusion. Accordingly the medicament or formulation advantageously further comprises (superoxide) free radical scavengers (such as vitamins C and E) and/or angiotensin converting enzyme (ACE) inhibitors and/or non-steroidal anti-inflammatory drugs such as aspirin, or ibuprofen and/or omega-3 polyunsaturated fatty acids (PUFAs) which are protected in a pharmacologically acceptable way against peroxidation.

The omega-3 PUFAs may be employed in free acid form, in a form suitable for the physiological supply of omega-3 PUFAs, e.g. in triglyceride form, or in the form of pharmacologically acceptable natural sources of omega-3 PUFAs. Such natural sources include linseed oil and fish oils such as menhaden oil, salmon oil, mackerel oil, tuna oil, codliver oil and anchovy oil. Said natural sources, in particular, the fish oils, comprise substantial amounts of omega-6 fatty acids. Where the omega-3 PUFAs are employed in triglyceride form, said triglycerides may comprise esters with other pharmacologically acceptable fatty acids.

Preferred omega-3 PUFAs include eicosapentaenoic acid (EPA) and docosahexaenoic acid (DHA), in free acid form, in triglyceride form or in form of natural sources having a high EPA and/or DHA content.

Whilst the medicament or formulation must be administered prior to surgery there is no reason why its administration may not optionally be continued post-operatively. Such optional use of the medicament will naturally depend on the circumstances of the individual, but it is supposed that the use could be conveniently continued during the entire period that the patient is hospitalized (up to 20 days), if not longer.

In a preferred embodiment the present invention provides the use of L-arginine, a precursor of L-arginine and/or physiologically acceptable salts thereof together with omega-3 PUFAs which are optionally protected in a pharmacologically acceptable way against peroxidation, in the preparation of a medicament or nutritional formulation for the amelioration of micro-circulatory hypo-perfusion, and/or the treatment or prophylaxis of hypoperfusion-reperfusion injury, in patients which have undergone elective surgery, characterized in that the medicament or nutritional formulation is pre-operatively administered to the patient.

In a further preferred embodiment the present invention provides the use of (i) a nitric oxide donor, and/or (ii) a substrate of the nitric oxide synthetase, and/or (iii) a precursor of the said substrate together with omega-3 PUFAs, in the preparation of a medicament or nutritional formulation for the amelioration of micro-circulatory hypo-perfusion, and/or the treatment or prophylaxis of hypoperfusion-reperfusion injury, in patients which have undergone elective surgery, characterized in that the medicament or nutritional formulation is pre-operatively administered to the patient.

It is particularly preferred that the substrate of the nitric oxide synthetase is L-arginine or a pharmaceutically acceptable salt thereof.

The medicament of formulation used according to the invention may (and preferably will) still further comprise other nutritionally advantageous components such as vitamins, minerals, trace elements, fibers (preferably soluble fibers) as well as nitrogen sources, carbohydrate sources and additional fatty acid sources.

Examples of suitable nitrogen sources include nutritionally acceptable proteins such as soy bean or whey derived proteins, caseinates, and/or protein hydrolysates. Suitable carbohydrate sources include sugars such as maltodextrins. Examples of suitable fatty acid energy supply sources include triglycerides, as well as di- and monoglycerides.

Examples of vitamins suitable for incorporation into the medicament of the invention include Vitamin A, Vitamin D, Vitamin K, folic acid, thiamin, riboflavin, Vitamin $B_6$, Vitamin $B_{12}$, niacin, biotin and panthotenic acid in pharmaceutically acceptable form.

Examples of mineral elements and trace elements suitable for incorporation into the medicament include sodium, potassium, calcium, phosphorous, magnesium, manganese, copper, zinc, iron, selenium, chromium, and molybdenum in pharmaceutically acceptable form.

In particular, the medicament or formulation will preferably comprise beta-carotene (Vitamin A), Vitamin E, Vitamin C, thiamine, and choline, in pharmaceutically acceptable form.

The term "soluble fiber" as used herein refers to fibers which are able to undergo substantial fermentation in the colon ultimately to produce short chain fatty acids. Examples of suitable soluble fibers include pectin, guar gum, locust bean gum, xanthan gum which may optionally be hydrolysed. For adults the total amount of soluble fibre per day will conveniently lie in the range of from 3 to 30 g.

The medicament or formulation is primarily intended for use as a dietary supplement. In such a case, the amount of energy supplied by it should not be too excessive, in order not to unnecessarily suppress the patients appetite. The supplement should conveniently comprise energy sources in an amount supplying from 600 to 1500 Kcal/day. The contribution of the nitrogen source, carbohydrate source and lipid source to the total daily caloric may vary within wide ranges. In preferred forms of the medicament or formulation, the carbohydrate source provides for 40 to 70% of the total energy supply and, the nitrogen and fatty acid source each for 15 to 30% of the total energy supply of the medicament.

The medicament or formulation may be formulated in a manner known per se, for example, by simple admixing of the ingredients.

The invention will be further understood by reference to the following examples. The low-flow, reflow model of liver perfusion is used to investigate the effects of L-arginine on reperfusion injury in the absence of the possible complications of blood elements. In this model, pericentral regions of the liver lobule are made anoxic by reducing the flow rate for an initial period of the perfusion. Subsequently, normal flow rates are restored resulting in an oxygen dependent reperfusion injury in the pericentral regions of the liver lobule.

EXAMPLE 1

"Low-flow Reflow of Liver Perfusion—Animal Model"

Animals and Diets

Male Sprague-Dawley rats weighing between 100–160 g are caged individually and given powdered diets containing 5% of weight as corn oil, encapsulated fish oil, or encapsulated fish oil with additional L-arginine in a blind design ad libitum for 12–19 days or a powdered diet containing 5% of weight as L-arginine for three days (Table 1). The diets are kept under nitrogen at 4° C., and fresh diets are provided daily. Food intake is assessed by weighing the diet remaining each day. Rats are fasted for 24h prior to liver perfusion.

Perfusion

Rats are anaesthetized with pentobarbital sodium (1 µl/g) before surgery and livers are removed surgically and perfused, via a cannula inserted into the portal vein, with Krebs-Henseleit bicarbonate buffer (pH 7.4, 37° C.) saturated with an oxygen-carbon dioxide (95:5) mixture in a non-recirculating system as is known in the art. After surgery, livers are perfused at flow rates of about 1 ml/g/min for 75 minutes (low-flow). Under these conditions, periportal areas are normoxic while adjacent pericentral regions are anoxic. Subsequently, livers are perfused at normal flow rates (4 ml/g/min) for 40 minutes (reflow). Oxygen concentration in the effluent perfusate is monitored continuously with a Teflon-shielded, Clark-type oxygen electrode. Oxygen uptake is calculated from the influent minus effluent concentration difference, the flow rate and the liver wet weight.

A three way stop-cock is inserted into the tubing just prior to the cannula entering the portal vein. A polyethylene tube (PE 240) is placed in the three way stop-cock perpendicular to the cannula entering the portal vein. Portal pressure is monitored by changes in the height of a water column during perfusion. The common bile duct is cannulated with polyethylene tubing (PE- 10; Clay Adams), and aliquots of bile are collected into tarred vials at 15-min intervals in the low-flow and at 10-min intervals during reflow periods. Rates of bile production are calculated from weight of bile, time intervals and the wet weight of the liver.

Assays

Lactate dehydrogenase (LDH) activity in the perfusate is determined using standard enzymic techniques, and Malondialdehyde (MDA) is assessed using thiobarbituric acid according to known methods. Briefly, three ml of perfusate is mixed thoroughly with a reagent containing 15% trichloroacetic acid, 0.375% thiobarbituric acid and 0.25 N hydrochloric acid and is heated for 15 minutes in a boiling water bath. After cooling, the absorbance at 535 nm of the supernatant is determined. MDA concentration in the perfusate is calculated by comparison with MDA standards. Rates of release of LDH and MDA are expressed per gram wet weight of the liver per hour.

To assess microcirculation in the liver, trypan blue is infused into the liver at the end of all experiments at a concentration of 0.2 mM. The time for the liver surface to turn evenly dark blue—which an indication of the state of the livers micro-circulation—is recorded. The results are subjected to statistical analysis where appropriate. Student's T-test or ANOVA are used with differences being considered significant at P<0.05 level.

Effects of Arginine Treatment on Hepatocellular Damage in a Low-flow Reflow Model Rat livers are perfused at flow rates around 1 ml/g/min for 75 minutes followed by reperfusion for 40 minutes at flow rates around 4 ml/g/min. Release of lactate dehydrogenase rates of bile production, rates of malondialdehyde release and portal pressure during both the low-flow and reflow periods are determined.

During the low flow period, LDH release is minimal (around 3 IU/g/h at 60 minute) in livers from corn oil and encapsulated fish-oil-treated rats and in rats fed a fish oil diet supplemented with L-arginine. When the flow rate was increased to 4 ml/g/min, however, LDH release increased gradually reaching a new steady-state value in about 30 minutes. Maximal LDH release during the reperfusion period was around 50 IU/g/h in livers from control rats, but values were reduced significantly by encapsulated fish-oil treatment, L-arginine treatment, or by a combined L-arginine and encapsulated fish-oil treatment to around 20 IU/g/h. Rates of bile production were around 12 µp/g/h at the end of low-flow period in corn oil controls, and were not significantly different in the encapsulated fish-oil (optionally supplemented with arginine) treated group. Maximal bile production increased to about 23 µl/g/h during the reflow period in controls, but the value reached 36 µl/g/h in livers from encapsulated fish-oil-treated rats. Oxygen uptake during reperfusion was 111, 119 and 93 µmol/g/h in livers from control rats, from encapsulated fish-oil-treated rats and from rats fed encapsulated fish oils supplemented with L-arginine, respectively (p>0.05, student's t-test). Taken together, reperfusion injury, which occurs when oxygen is re-introduced into previously anoxic liver, is minimized by pre-feeding rats a diet supplemented with fish-oil and arginine.

Effect of Arginine Pre-feeding on Malondialdehyde Production

MDA, an end product of lipid peroxidation, is released into the effluent perfusate at rates around 15 nmol/g/h during 75 minutes of low-flow perfusion in livers from corn oil-fed, encapsulated fish-oil-fed, L-arginine and encapsulated fish-oil plus arginine fed rats. When flow rates were restored to normal, MDA production increased rapidly to peak values in about 15 minutes and then decreased slightly. Maximal MDA production during the reperfusion period was around 90 nmol/g/h in control rats, 80 nmol/g/h in encapsulated fish-oil-treated rats, 45 nmol/g/h in L-arginine-treated rats and 67nmol/g/h in rats pre-fed encapsulated fish oil supplemented with arginine, respectively, the differences between the various groups not being statistically significant.

Effect of Arginine Pre-feeding on Trypan Blue Distribution Time

Trypan blue distribution time is an indicator of the hepatic microcirculation. It took 10.7 minutes for trypan blue to distribute evenly in livers from corn-oil-treated rats, 6.0 minutes in the case of rats pre-fed with encapsulated fish-oils, 3.8 minutes in the case of rats pre-fed with L-arginine and 2.8 minutes for rats pre-fed with encapsulated fish-oils supplemented with arginine. These results are extremely significant (p<0.05, Student's T Test).

The above description (the results of which are summarized in Table 2) clearly indicates that pre-feeding with an arginine rich diet provides for an improved microcirculation in organs likely to be subject to hypoperfusion-reperfusion injury, and that this protective effect of arginine is apparent even though the diet is curtailed prior to surgery.

One of the consequences of elective surgery (as well as accident surgery for that matter) is a partial shut-down of the micro-circulations associated with the liver and heart, but particularly the mesentery/gut. This "shut-down" facilitates metabolic changes associated with such micro-circulations which provides for free radical damage, particularly by superoxide anions, upon their subsequent reperfusion. Such free radical damage may render the gut microcirculation leaky to products of digestion, in particular bacterial cell components. Such components may enter the general circulation and subsequently initiate (endo)toxic shock syndromes which are manifest post-operatively, and the consequences of which may be fatal. In the above Example the rats were starved for 24 hours prior to liver perfusion. This "starvation" mimics that which is experienced by patients prior to elective surgery. It is thus clear that the pre-feeding of humans with a medicament or nutritional formulation which comprises L-arginine can be expected to have a prophylactic effect vis à vis the hypoperfusion-reperfusion injury that is otherwise experienced post-operatively. The practical significance of such prophylaxis, especially in the case of the mesenteric/gut micro-circulations, cannot be overstated.

TABLE 1

Composition of (corn oil based) control and encapsulated fish oil, optionally containing arginine, diets.

| | % (W/W) | | | |
|---|---|---|---|---|
| Component | control | fish oil | fish oil + arginine | arginine |
| ICN Casein | 15.0 | 15.0 | 14.0 | 14.0 |
| arginine | | | 5.0 | 5.0 |
| Sucrose | 51.0 | 40.0 | 38.0 | 40.0 |
| Corn oil | 5.0 | — | — | 5.0 |
| Fish oil (encapsulated) | — | 5.0 | 5.0 | — |
| Capsules | — | 20.0 | 20.0 | — |
| AIN mineral mixture | 3.5 | 3.5 | 3.5 | 3.5 |
| AIN Vitamin mixture | 1.0 | 1.0 | 1.0 | 1.0 |
| DL-methionine | 0.3 | 0.3 | 0.3 | 0.3 |
| Choline bitartrate | 0.2 | 0.2 | 0.2 | 0.2 |
| Corn starch | 15.0 | 16.0 | 8.0 | 15.0 |
| Gum Arabic | 4.0 | 5.0 | — | 5.0 |

The encapsulated fish-oil is in triglyceride form, with an EPA:DHA ratio of 18:12. The fatty acid content is as follows:-

| | |
|---|---|
| omega-3 fatty acids including EPA 18% of fish oil DHA 12% of fish oil Docosapentaenoic acid (DPA) 2% of fish oil others 3% of fish oil | 35% |
| polyunsaturated fatty acids other than omega-3 | 11% |
| monounsaturated fatty acids | 28% |
| saturated fatty acids | 26% |

(% are by weight)

The mineral mixture comprises:

Mineral

| | | |
|---|---|---|
| Calcium | % w/w diet | 0.50 |

TABLE 1-continued

Composition of (corn oil based) control and encapsulated fish oil, optionally containing arginine, diets.

| | | |
|---|---|---|
| Chloride | % w/w diet | 0.05 |
| Magnesium | % w/w diet | 0.04 |
| Phosphorus | % w/w diet | 0.40 |
| Potassium | % w/w diet | 0.36 |
| Sodium | % w/w diet | 0.05 |
| Sulfur | % w/w diet | 0.03 |
| Chromium | mg/kg diet | 0.30 |
| Copper | mg/kg diet | 3.00 |
| Fluoride | mg/kg diet | 1.00 |
| Iodine | mg/kg diet | 0.15 |
| Iron | mg/kg diet | 35.00 |
| Manganese | mg/kg diet | 50.00 |
| Selenium | mg/kg diet | 0.10 |
| Zinc | mg/kg diet | 12.00 |

The vitamin mixture comprises per kg diet:

| | | |
|---|---|---|
| $A^{(1)}$ | 4000.00 | IU |
| $D^{(2)}$ | 1000.00 | IU |
| $E^{(3)}$ | 30.00 | IU |
| $K_1$ | 50.00 | µg |
| Choline | 1000.00 | mg |
| Folic acid | 1.00 | mg |
| Niacin | 20.00 | mg |
| Pantothenate (calcium) | 8.00 | mg |
| Riboflavin | 3.00 | mg |
| Thiamin | 4.00 | mg |
| Vitamin $B_6$ | 6.00 | mg |
| Vitamin $B_{12}$ | 50.00 | µg |

[1] Vitamin A: 1 IU = 0.500 µg retinol
[2] Vitamin D, 1 IU = 0.025 µg ergocalciferol
[3] Vitamin E, 1 IU = 1 mg DL-α-tocopheryl acetate.

TABLE 2

Effects of fish oil and fish oil and arginine containing diet on the microcirculation of perfused rat livers.

| | Corn Oil | | Fish Oil | | arginine | | Fish Oil + arginine | |
|---|---|---|---|---|---|---|---|---|
| Parameter | low flow | reflow | low flow | reflow | low flow | reflow | low flow | reflow |
| LDH IU/g/h | 3 (n = 6) | 51 (n = 6) | 2 (n = 6) | 17 (n = 6) | 4 (n = 10–13) | $24^1$ (n = 10–13) | 3 (n = 5) | 23 (n = 5) |
| MDA nmol/g/h | 15 (n = 6) | 90 (n = 6) | 15 (n = 6) | 80 (n = 6) | 8 (N = 5–7) | $45^2$ (n = 5–7) | 15 (n = 5) | 67 (n = 5) |
| Bile flow µl/g/h | 12 (n = 6) | 23 (n = 6) | 16 (n = 6) | 36 (n = 6) | | | 11 (n = 4) | 25 (n = 4) |
| $O_2$ µmol/g/h | 111 (n = 6) | | 119 (n = 6) | | | | 93 (n = 5) | |
| TB (minutes) | 10.7 (n = 6) | | 6.0 (n = 6)$^1$ | | 3.8 (n = 4) | | 2.8 (n = 4)$^2$ | |

$^2$p < 0.05 versus corn oil and fish oil diet
$^1$p < 0.05 versus corn oil diet

9
EXAMPLE 2

"Patient Study"

To evaluate whether preoperative administration of a supplemented enteral formula (see Table 3) results in an improvement of the microcirculation in patients undergoing to elective major abdominals surgery, intraoperative mesenteric blood flow (with doppler) at laparotomy and at the end of surgery, and intraoperative mucosa pHi and oxygenation (tonometry) at laparotomy and at the end of surgery were measured. Monitoring of the gastrointestinal mucosal perfusion by tonometry during major surgery and early after trauma appear to be a very sensitive method to predict the developments of organi failure and poor outcome. It has been repeatedly shown that patients with low postinjury pHi have high risk of morbidity and mortality.

The study included 40 patients who were be submitted to radical surgery for gastric, pancreatic and colorectal cancer. Patients were randomised in two groups: Group A—which received preoperative enteral supplemented formula via the oral route for 7 days before surgery plus postoperative nutrition from the end of operation for 7 days and Group B—which received a preoperative enteral control diet via a oral route for 7 days before surgery plus postoperative nutrition from the end of operation for 7 days. The composition of the diets is reported in Table 3.

Patients drank 1 liter of either supplemented enteral formula or control formula per day (for 7 days before surgery), corresponding to 1000 kcal/day, and they were allowed to eat a standard diet contemporaneously. Postoperatively the two groups received the same energy (25 kcal/kg/day) and nitrogen (0.25 g N/kg/day) intake.

Plasma arginine levels 1 day before surgery were at about 65±20 µmol/l for Group B and at about 105±46 µmol/l for Group A.

TABLE 3

Composition of the diets (per 100 ml)

|  | Preoperative formulas | | Preoperative formulas | |
| --- | --- | --- | --- | --- |
|  | Supplemented | Control | Supplemented | Control |
| Total proteins (g) | 5.6 | 4.35 | 5.6 | 5.6 |
| Free L-arginine (g) | 1.25 | — | 1.25 | — |
| L-Serine (g) | — | — | — | 0.93 |
| L-Glycine (g) | — | — | — | 0.77 |
| L-Alanine (g) | — | — | — | 0.51 |
| L-Proline (g) | — | — | 0.12 | — |
| RNA (g) | 0.12 | — | 0.12 | — |
| Total lipids (g) | 2.8 | 2.8 | 2.8 | 2.8 |
| n-3-fatty acids (%) | 10.5 | — | 10.5 | — |
| n-6-fatty acids (%) | 8.3 | 35.7 | 8.3 | 24.1 |
| Carbohydrates (g) | 13.3 | 14.5 | 13.4 | 13.4 |
| Total energy (kcal) | 101 | 101 | 101 | 101 |
| Osmolarity (mosm/L) |  |  | 293 | 486 |

The measurement of intraoperative intestinal microperfusion as measured by Laser-doppler is given in the following Table 4:

TABLE 4

Laser-doppler measurement of blood flow in perfusion units (PU):

| Diet | Ileum Baseline | End | Colon Baseline | End |
| --- | --- | --- | --- | --- |
| Supplemented | 180 ± 46*† | 154 ± 55* | 135 ± 31*† | 117 ± 32* |
| Standard | 146 ± 59† | 121 ± 48 | 112 ± 29† | 92 ± 30 |

\*vs. Standard
†vs. End

Jejunal mucosal pH and postoperative tonometry is given in the following Table 5:

TABLE 5

Postoperative Tonometry, measurement of intestinal mucosa oxygen metabolism pHi:

| Diet | Day 1 | Day 4 | Day 7 |
| --- | --- | --- | --- |
| Supplemented | 7.39 ± 0.23* | 7.41 ± 0.16* | 7.40 ± 0.12 |
| Standard | 7.33 ± 0.18 | 7.36 ± 0.21 | 7.38 ± 0.10 |

\*$p < 0.05$ vs. Control

Although an adequate blood flow is no guarantee of a good tissue oxygen tension, delivery and utilization, the date given above shows that a higher intestinal microperfusion, as directly measure by laser Doppler flowmetry technique, paralleled a better gut mucosal oxydative metabolism.

Whilst the invention has been particularly described with respect to the above specific examples, the skilled man will understand that the invention is not limited to this but includes all logical developments.

For example, the invention further provides the use of L-arginine, a precursor of L-arginine and/or physiologically acceptable salts thereof, or of a nitric oxide donor, and/or a substrate of the nitric oxide synthetase, and/or a precursor of the said substrate in the preparation of a medicament or nutritional formulation for the prevention and/or reduction of neutrophil activation or adherence, or the prevention and/or reduction of superoxide anion mediated free radical damage, in patients which have undergone elective surgery, characterized in that the medicament or formulation is pre-operatively administered to the patient.

We claim:

1. A method for modulating microcirculation in a patient in need of such modulation comprising administering pre-operatively to a patient undergoing surgery to the patient a composition comprising an effective microcirculation modulating amount of L-arginine, a precursor of L-arginine and/or physiologically acceptable salts thereof, and a nutritionally acceptable carrier.

2. A method for the amelioration of microcirculatory hypoperfusion, and/or the treatment or prophylaxis or hypoperfusion-reperfusion injury, in patients in need of such amelioration, treatment or prophylaxis, comprising administering preoperatively to a patient undergoing surgery to the patient a composition comprising an effective amount of a nitric oxide donor and/or a substrate of nitric oxide synthetase and/or a precursor of the substrate, for the amelioration, treatment or prophylaxis, and a nutritionally acceptable carrier.

3. The method according to claim 2, wherein the nitric oxide substrate is L-arginine or a physiologically acceptable salt thereof.

4. The method according to claim 2, wherein the precursor of L-arginine is ornithine or glutamine.

5. The method according to claim 2, wherein the administration is initiated at least one day prior to surgery.

6. The method according to claim 5, wherein the administration is initiated between 3–10 days prior to surgery.

7. The method according to claim 2, wherein the composition is administered enterally, orally, and/or parenterally.

8. The method according to claim 2, wherein the composition comprises, as a daily dose, about 1–30 g of a nitric oxide substrate.

9. The method according to claim 8 wherein the nitric oxide substrate comprises L-arginine.

10. The method according to claim 2 wherein the composition comprises, as a daily dose, about 1–30 g of a precursor of L-arginine and/or physiologically acceptable salts thereof.

11. The method according to claim 10 wherein the precursor comprises ornithine or glutamine.

12. The method according to claim 2 wherein the composition comprises, in a daily dose, about 0.1 to 20 g of a nitric oxide donor.

13. The method according to claim 2 wherein the composition is administered to the patient in an amount such that the total concentration of nitric oxide substrate or L-arginine, precursor of L-arginine and/or physiologically acceptable salts thereof, in the patient's plasma is from about 100 to about 200 µM.

14. The method according to claim 2, wherein the donor is selected from the group consisting of glycerol trinitrate, isosorbide dinitrate, nitroprusside, 8-bromoguanosine-3,5'-monophosphate, spermine-NO, spermidine-NO, and SIN1.

15. The method according to claim 2 wherein the composition further comprises at least one additive selected from the group consisting of superoxide free radical scavengers, angiotensin converting enzyme inhibitors, nonsteroidal anti-inflammatory compounds, omega-3 polyunsaturated fatty acids which are protected in a pharmacologically acceptable way against peroxidation, vitamins, mineral elements, soluble fibre, caseinates and protein hydrolysates and omega-6 polyunsaturated fatty acids.

16. A method for the prevention or reduction of neutrophil activation and/or adherence to the mesentery or gut, or the prevention or reduction of superoxide anion mediated free radical damage, in a patient who has undergone surgery, comprising pre-operatively administering to the patient a composition comprising L-arginine, a precursor of L-arginine and/or physiologically acceptable salts thereof, a nitric oxide donor, and/or a substrate of nitric oxide synthetase, and/or a precursor of the substrate, and a nutritionally acceptable carrier.

17. The method according to claim 2 wherein the composition further comprises omega-3 polyunsaturated fatty acids which are optionally protected in a pharmacologically acceptable way against peroxidation.

* * * * *

UNITED STATES PATENT AND TRADEMARK OFFICE
CERTIFICATE OF CORRECTION

PATENT NO.    : 5,902,829
DATED         : May 11, 1999
INVENTOR(S)   : Heinz Schneider It is certified that error appears in the above-identified patent and that said Letters Patent is hereby corrected as shown below:

<u>Title page,</u>
Item [75], kindly remove "Ronald G. Thurman" as Inventor.

Signed and Sealed this

Twenty-ninth Day of April, 2003

JAMES E. ROGAN
*Director of the United States Patent and Trademark Office*